US00PP31993P2

(12) United States Plant Patent
van Geest

(10) Patent No.: US PP31,993 P2
(45) Date of Patent: Jul. 21, 2020

(54) ***FICUS* PLANT NAMED 'ESPE1901'**

(50) Latin Name: *Ficus benghalensis*
Varietal Denomination: ESPE1901

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/501,281

(22) Filed: Mar. 16, 2019

(51) Int. Cl.
*A01H 5/00* (2018.01)
*A01H 6/00* (2018.01)

(52) U.S. Cl.
USPC ..... Plt./211

(58) Field of Classification Search
USPC ..... Plt./211
CPC ... A01H 5/00; A01H 5/08; A01H 5/12; A01H 6/00
See application file for complete search history.

*Primary Examiner* — June Hwu
(74) *Attorney, Agent, or Firm* — Samuel R. McCoy, Jr.

(57) ABSTRACT

A new and distinct variety of *Ficus* plant named 'ESPE1901' which is characterized by the combination of large leaves held upright on a medium-sized plant, dark green leaves with prominent light green venation, and the stability of all characteristics from generation to generation.

3 Drawing Sheets

Latin name of the genus and species: The Latin name of the genus and species of the novel variety disclosed herein is *Ficus benghalensis.*

Variety denomination: The inventive variety of *Ficus* disclosed herein has been given the variety denomination 'ESPE1901'.

BACKGROUND OF THE INVENTION

Parentage: 'ESPE1901' originated as a naturally occurring, whole-plant mutation of an unnamed *Ficus benghalensis* plant (not patented). In February of 2014, the inventor discovered the mutation at his commercial greenhouse in Gravenzande, The Netherlands, growing amongst a cultivated population of *Ficus benghalensis* plants. The mutation was noted for its large, dark green leaves with prominent light green venation and was subsequently isolated for further evaluation in order to confirm the distinctness and stability of the characteristics first observed. Upon confirmation of distinctness and stability, 'ESPE1901' was selected for commercialization.

Asexual Reproduction: Asexual reproduction of ESPE1901', by way of stem cuttings, was first initiated in the summer of 2014 at a commercial greenhouse in Gravenzande, The Netherlands. Through five subsequent generations, the unique features of this cultivar have proven to be stable and true to type.

SUMMARY OF THE INVENTION

The cultivar 'ESPE1901' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESPE1901'. These characteristics in combination distinguish 'ESPE1901' as a new and distinct *Ficus* cultivar:

1. *Ficus* 'ESPE1901' exhibits large leaves held upright on a medium-sized plant; and
2. *Ficus* 'ESPE1901' exhibits dark green leaves with prominent light green venation, particularly on the abaxial leaf surface.

BOTANICAL DESCRIPTION OF THE PLANT

Figure 1:
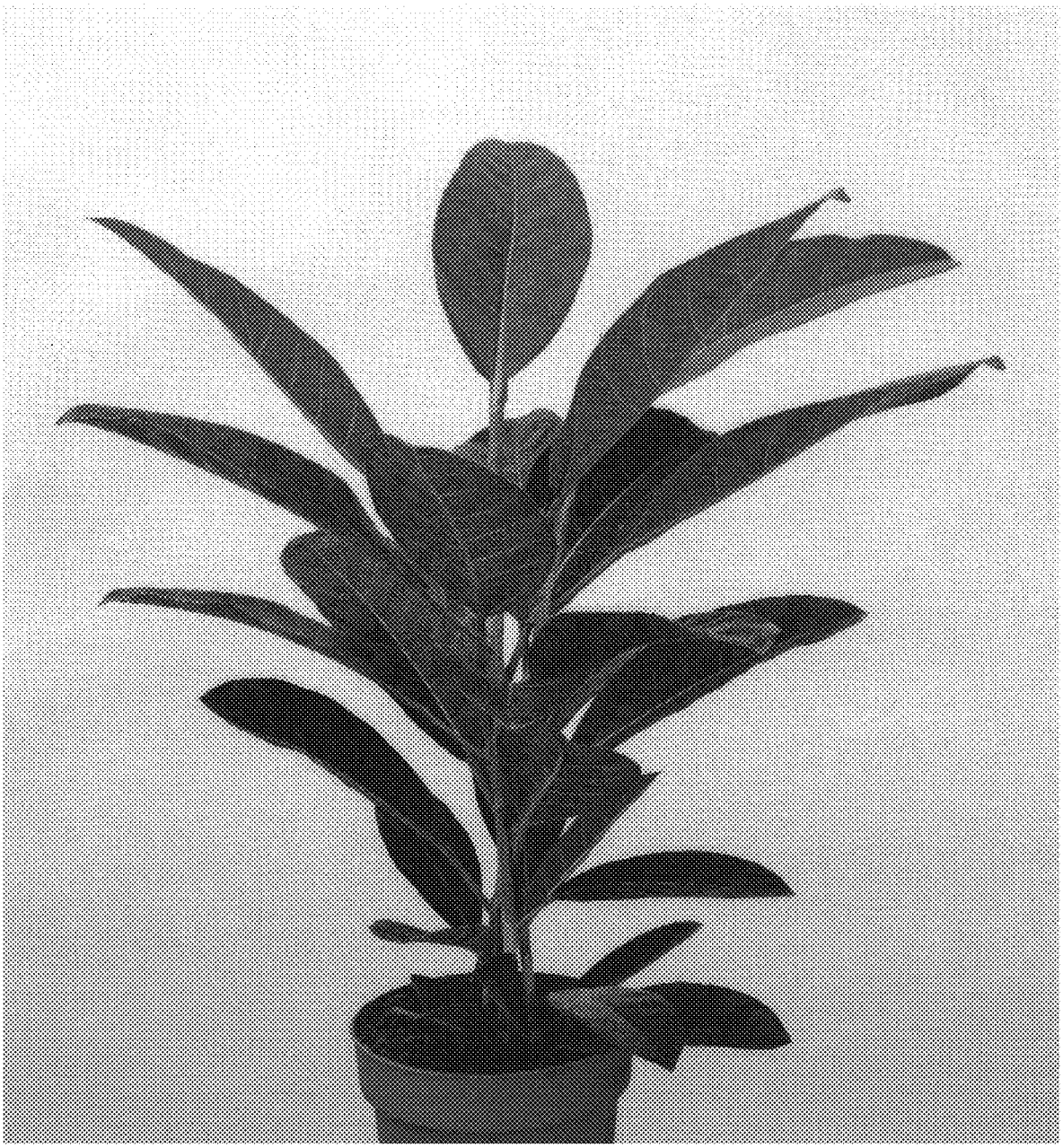
FIG. 1 illustrates, as nearly true as it is reasonably possible to make the same in color photographs of this type, an exemplary plant of 'ESPE1901' grown in a commercial greenhouse in Gravenzande, The Netherlands. This plant is approximately 25 weeks old, shown planted in a 19 cm container.
Figure 2:
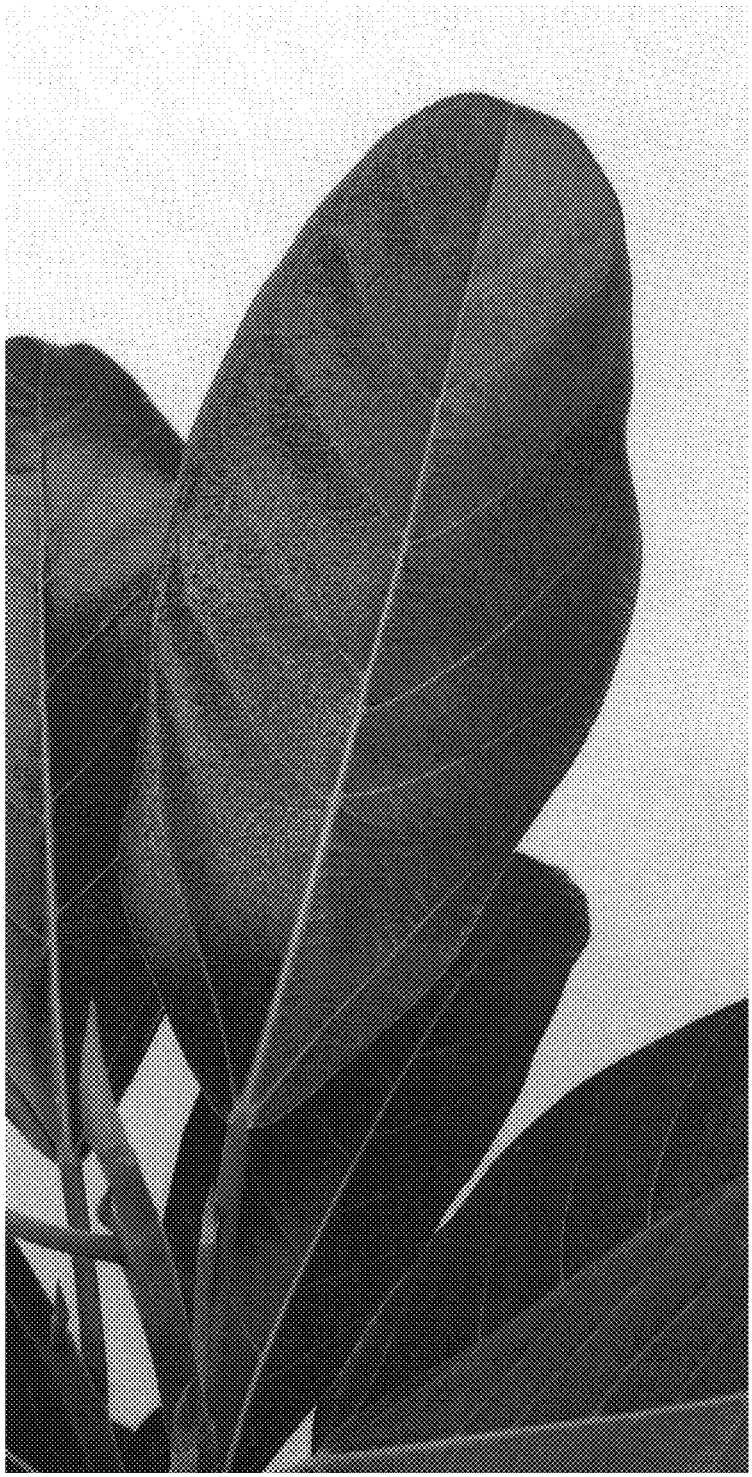
FIG. 2 illustrates, as nearly true as it is reasonably possible to make the same in color photographs of this type, the adaxial surface of the mature foliage of 'ESPE1901'.
Figure 3:
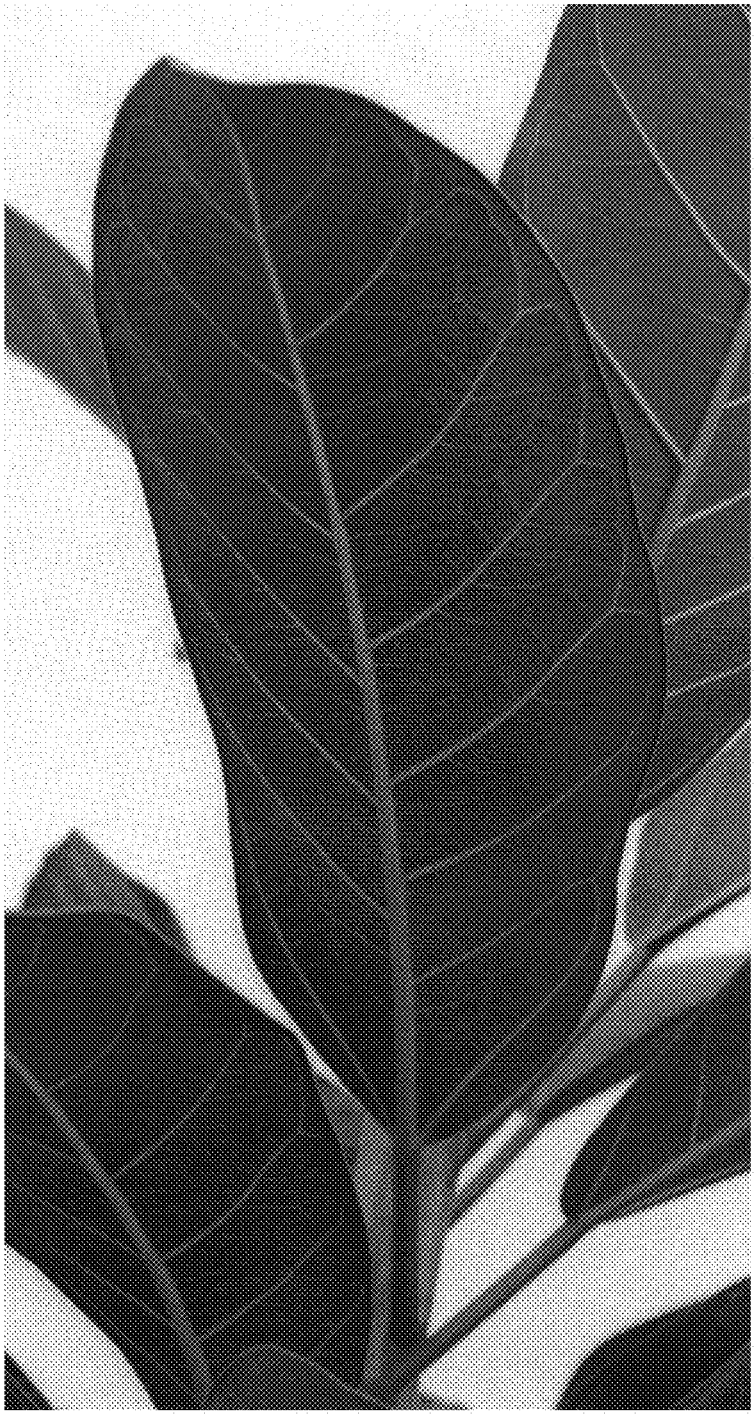
FIG. 3 illustrates, as nearly true as it is reasonably possible to make the same in color photographs of this type, the abaxial surface of the mature foliage of 'ESPE1901'.

The following observations and measurements were made in February of 2019 and describe a sample set of six 25 week-old 'ESPE1901' plants grown in 19 cm nursery pots, two plants per container, at a greenhouse in Gravenzande, The Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESPE1901' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'ESPE1901' and comparisons with the parent plant and most similar commercial variety of *Ficus* are provided below.

Plant description:

*Growth habit.*—Upright broadleaf evergreen tree.

*Plant form.*—Broad oblong.

*Average height.*—67.0 cm from the soil level to the top of the foliar plane.

*Plant spread.*—Average of 61.5 cm.

*Growth rate.*—Moderately fast to fast.

*Plant vigor.*—Moderately vigorous to vigorous.

*Propagation type.*—Stem cuttings.

*Time to produce a rooted cutting.*—Approximately 40 days to produce a rooted cutting at approximately 25 degrees Celsius.

*Time to produce a finished plant.*—Approximately 18 weeks to produce a marketable finished plant in a 17 cm pot.

*Disease resistance.*—Neither resistance nor susceptibility to typical *Ficus benghalensis* pests and diseases has been observed.

*Environmental tolerances.*—Adapt to, at least, USDA Zones 10 through 13 and temperatures as high as 40 degrees Celsius; moderate to high tolerance to rain; low to moderate tolerance to wind.

Root system:

*General.*—Moderately dense, moderately branched rooting; roots are slightly fibrous.

*Distribution in the soil profile.*—Moderately deep.

*Diameter of roots.*—1.25 mm on average.

*Texture.*—Smooth; no root hairs.

*Color.*—Greyed-orange, nearest to RHS 163A. Young roots are colored greyed-yellow, nearest to RHS 162B.

Stem:

*General branching habit.*—Basally branching main stems; no lateral branching. Pinching isn't required but will improve branching. Stems produce a milky exudate when damaged.

*Quantity of stems.*—3.

*Length.*—Approximately 50.1 cm.

*Diameter.*—Approximately 0.9 cm.

*Internode length.*—Approximately 6.4 cm.

*Attitude.*—Near vertical.

*Aspect.*—Rounded.

*Texture.*—Young stems are covered with a crackled scape-like pubescence which is colored greyed-green, nearest to RHS 197D. Mature stems are densely covered with very short soft hairs with an average length of 0.3 mm. Hairs are colored greyed-brown, nearest to RHS 199D.

*Luster.*—Matte.

*Strength.*—Strong.

*Color, juvenile.*—Yellow-green, nearest to RHS 144A.

*Color, mature.*—Yellow-green, nearest to RHS 148A.

*Color at internodes.*—Yellow-green, nearest to RHS 148A, and radially striped greyed-orange, nearest to RHS 172A.

*Color of the oldest wood.*—Greyed-brown, nearest to a mixture of RHS 199C and 199D, and axially striped darker, nearest to a mixture of RHS N199C and N199D.

Foliage:

*Arrangement.*—Alternate.

*Division.*—Simple.

*Quantity.*—8 leaves per lateral branch.

*Attitude.*—At an average angle of 40 degrees to the branch.

*Lamina.*—Shape — Elliptic. Aspect — Slightly carinate. Dimensions — 27.8 cm long and 12.1 cm wide. Apex — Short apiculate with a blunt tip. Base — Cuneate. Margin — Entire; very slightly undulate. Texture and luster of the adaxial surface — Smooth and densely covered with very short green-white hairs, nearest to RHS 157D, with an average length of 0.3 mm. Texture of the abaxial surface — Slightly rugose and densely covered with very short green-white hairs, nearest to RHS 157D, with an average length of 0.3 mm. Luster of the adaxial surface — Moderately glossy. Luster of the abaxial surface — Matte. Color — Juvenile foliage, adaxial surface — Green, nearest to RHS NN137A, and veined yellow-green, nearest to RHS N144D. Juvenile foliage, abaxial surface — Yellow-green, nearest to in between RHS 144A and 146B, and veined lighter, nearest to in between RHS 145A and 150B. Mature foliage, adaxial surface — Nearest to in between green and yellow-green, RHS NN137A and 147A. Mature foliage, abaxial surface — Yellow-green, nearest to in between RHS 146B and 147B.

*Venation.*—Pattern — Pinnate. Color, adaxial surface — Yellow-green, nearest to RHS N144D. Color, abaxial surface — Yellow-green, nearest to RHS 145A.

*Stipule.*—Not present.

*Petiole.*—Length — 5.2 cm. Diameter — 0.6 cm. Strength — Strong. Texture — Densely covered with soft green-white hairs, nearest to RHS 157D, with an average length of 0.5 mm. Luster — Matte. Color: adaxial surface — Yellow-green, nearest to RHS 146B. Color, abaxial surface — Yellow-green, nearest to RHS 144A.

Inflorescence: No flowering has been observed to date.

Comparison with the parent plant: Plants of the new cultivar 'ESPE1901' differ from the parent, an unnamed *Ficus benghalensis* plant (not patented), in the following characteristics described in Table 1 below.

TABLE 1

| Characteristic | 'ESPE1901' | The parent |
|---|---|---|
| Stem length. | Shorter than the parent. | Longer than 'ESPE1901'. |
| Foliage abundance. | Less abundant than the parent. | More abundant than 'ESPE1901'. |
| Foliage attitude. | More upright. | More relaxed. |
| Foliage size. | Larger than the parent. | Smaller than 'ESPE1901'. |
| General coloration of the mature foliage. | Darker green. | Lighter green. |

Comparison with the closest known comparator: Plants of the new cultivar 'ESPE1901' differs from the variety, *Ficus bussei* 'ESFIBU1802' (U.S. Patent application Ser. No. 16/501,282), for which a United States plant patent application is being filed concurrently with the instant application, in the following characteristics described in Table 2 below.

TABLE 2

| Characteristic | 'ESPE1901' | 'ESFIBU1802' |
|---|---|---|
| Foliage shape. | Elliptic. | Ovate. |
| Foliage attitude. | More upright than ESFIBU1802'. | More relaxed than 'ESPE1901'. |

TABLE 2-continued

| Characteristic | 'ESPE1901' | 'ESFIBU1802' |
|---|---|---|
| Foliage venation. | Less densely pinnate. | More densely pinnate. |
| Foliage margin undulation. | Very slightly undulated. | Slightly angulate; moderately undulate. |

That which is claimed is:

1. A new and distinct variety of *Ficus* plant named 'ESPE1901', substantially as described and illustrated herein.

* * * * *